United States Patent [19]

Narita et al.

[11] Patent Number: 5,101,663
[45] Date of Patent: Apr. 7, 1992

[54] METHOD FOR THE DETERMINATION OF STRENGTH OF JOIN BETWEEN CERAMIC AND NON-CERAMIC

[75] Inventors: Toshio Narita, Sapporo; Isao Ishikawa, Tsuchiura; Tatuo Ishikawa, Sapporo, all of Japan

[73] Assignee: Hitachi Construction Machinery Co., Ltd., Chiyoda, Japan

[21] Appl. No.: 735,663

[22] Filed: Jul. 26, 1991

Related U.S. Application Data

[63] Continuation of Ser. No. 509,371, Apr. 17, 1990, abandoned.

[30] Foreign Application Priority Data

Apr. 17, 1989 [JP] Japan .................................. 1-95248
Mar. 23, 1990 [JP] Japan .................................. 2-71853

[51] Int. Cl.$^5$ .......................................... G01N 29/04
[52] U.S. Cl. ........................................ 73/588; 73/606
[58] Field of Search ............... 73/588, 596, 606, 607, 73/620, 627, 629, 827

[56] References Cited

U.S. PATENT DOCUMENTS

| 4,366,713 | 1/1983 | Gilmore et al. | 73/588 |
| 4,524,621 | 6/1985 | Yamanaka | 73/606 |
| 4,655,083 | 4/1987 | Chubachi | 73/606 |
| 4,730,494 | 3/1988 | Ishikawa et al. | 73/606 |

FOREIGN PATENT DOCUMENTS 3043794 3/1982 Fed. Rep. of Germany .

OTHER PUBLICATIONS

Ultrasonic Scanning & Spectrum Analysis for Inspection of Bond Efficiency of Metal–Metal Structural Adhesive Joints by G. Biggiero et al. NDT International, Apr. 1983.

Ultrasonic Nondestructive Bond Evaluation: An Analysis of the Problem, by H. H. Chaskelis et al., Mat. Eval. Apr. 1980.

Patent Abstracts of Japan, vol. 10, No. 274 (P-498)(2330), 18 Sep. 1986; & JP-A-61096452 (Agency of Ind. Science & Technol.) May 15, 1986.

Electronics Letters, vol. 19, No. 14, Jul. 1983, pp. 512-514, London, GB; J. Kushibiki, title: Attenuaton measurements of leaky waves by the acoustic line-focus beam (entire article).

Automatic Welding, vol. 37, No. 10, Oct. 1984, pp. 56-57, Cambridge, GB; O. I. Gushcha, title: Certain features of the measurement of stresses by the acoustic method (entire article).

*Primary Examiner*—Hezron E. Williams
*Assistant Examiner*—Louis M. Arana
*Attorney, Agent, or Firm*—Wegner, Cantor, Mueller & Player

[57] ABSTRACT

The strength of a join between a ceramic and an associated non-ceramic is determined using an ultrasonic microscope. A converging ultrasonic beam is radiated against a point on a surface of the ceramic, said point being a predetermined distance away from the join between the ceramic and the associated non-ceramic. Data on the intensities of interference waves at respective predetermined variations of the relative distance between a probe of the ultrasonic microscope and the ceramic are collected. The residual stress at the point is calculated on the basis of the cycle of echo intensities of the interference waves for the respective predetermined variations of the relative distance. The strength of the join is then determined on the basis the residual stress.

3 Claims, 3 Drawing Sheets

METHOD FOR THE DETERMINATION OF STRENGTH OF JOIN BETWEEN CERAMIC AND NON-CERAMIC

This application is a continuation of U.S. application Ser. No. 07/509,371, filed Apr. 17, 1990, now abandoned.

BACKGROUND OF THE INVENTION a) Field of the Invention

The present invention relates to a method for determining the strength of a join between a ceramic and a non-ceramic.

b) Description of the Related Art

Ceramics have excellent material characteristics in hardness, abrasion resistance, corrosion resistance and the like, and are expected to find utility as principal equipment materials in many fields from now on. These fields include some where ceramics may be used as discrete members, parts or components (hereinafter collectively called "members"), but ceramics are also expected to be employed in forms where they are joined with one or more other members in many other fields. Especially in the field of mechanical or structural members, ceramics will be used in a form where they are joined with a metal.

A ceramic is different in coefficient of thermal expansion and modulus of elasticity from a metal, so that when they are joined together, a residual stress is produced in the ceramic and the strength of the resulting body so joined is governed by the residual stress. To form a good joined body, it is therefore indispensable to ensure joining results in minimal residual stress. A variety of joining methods have hence been attempted. FIG. 1 is a side view of a joined ceramic-Kovar (trade mark) body, illustrating one of such joining methods. In the drawing, there are depicted a ceramic 1, Kovar 2, and an intermediate nickel material 3. It has been reported that the joining of the ceramic 1 and Kovar 2 by using the intermediate material as shown in the drawing leads to increased strength of the ceramic 1 at the join compared with their direct joining and the strength varies depending on the thickness of the intermediate nickel layer 3.

The quality of each joining method for a ceramic and a non-ceramic is determined by measuring the residual stress. Examples of this measurement include a method for calculating such residual stress by using the finite element method, conventional X-ray diffraction, IF (indentation fracture) technique, laser spectroscopy, etc.

However, the above calculation of residual stress in a ceramic by the infinite element method is complex and time-consuming, so that this measurement method cannot be used for the inspection of dispersion or the like of actual products. On the other hand, X-ray diffraction, IF technique and laser spectroscopy involve one or more problems as will be discussed below.

Because a ceramic is a sintered material, the residual stress produced at a join between the ceramic and a non-ceramic has a more complex distribution compared with the residual stress produced at a join between non-ceramics. Further, the residual stress in the former case has a stronger tendency to concentrate on the outer surface of the join, whereby the residual stress changes abruptly depending on the position. With reference to a drawing, a description will next be made of one example of stress distribution which occurs in a typical ceramic/non-ceramic joined body.

FIG. 2 is a stress distribution diagram of a joined ceramic-metal body which makes use of an intermediate nickel material. In this diagram, $Si_3N_4$ and (W/Ni)/Fe-30Cr are used as the ceramic and the metal, respectively. Distances (mm) from the joined end surface of the ceramic on the side of the ceramic are plotted along the axis of abscissas, while stresses (MPa) are plotted along the axis of ordinates. Curves A, B and C correspond respectively to joined bodies in which the thicknesses of the respective intermediate nickel layers are 2.0 mm, 1.25 mm and 0.5 mm. The following can be envisaged from the diagram. In the joined body C, tensile stress exists throughout the ceramic. In particular, tensile stress reaches as great as 600 MPa around the interface between the ceramic and metal. In the joined body A on the other hand, tensile stress is developed at the ceramic-metal interface but this tensile stress decreases with the distance from the interface. After compressive stress is developed once, tensile stress is produced again. This tensile strength reaches a maximum value and then decreases gradually. Turning next to the joined body B, the distribution pattern of stress is similar to that of the joined body A but the stress is not greater than 200 MPa.

As is shown in the stress distribution diagram described above, the distance-dependent stress variations of the joined body C are relatively gentle but those of the joined bodies A and B are complex and steep. Accordingly, the measurement of stress in a small region in the order of $\mu m$ is apparently indispensable for the determination of accurate stress distribution.

The conventional measurement methods, namely, X-ray diffraction, IF technique and laser spectroscopy are however unable to conduct measurement in such a small region. As a consequence, measurement by such a conventional method covers a substantially wide region. The measurement therefore provides, as the result, an average value of residual stress across a wide region. It is by no means possible to obtain an accurate stress distribution diagram. Moreover, breakage of a ceramic takes place at once from the point where the residual stress is maximum. This maximum value of residual stress may be overlooked as long as such an average value as described above is relied upon, leading to the problem that the resulting stress distribution diagram is extremely inconvenient for practical applications.

SUMMARY OF THE INVENTION

An object of the present invention is therefore to overcome the above-described problems of the conventional methods and to provide a method for the determination of the strength of a join between a ceramic and a non-ceramic, which method makes it possible to measure stress in a small region of the ceramic and thus to accurately determine the strength of the join.

With a view toward attaining the above object, the present inventors are firstly interested in the phenomenon that a residual stress developed in a ceramic upon formation of a joined body with the ceramic and another material, i.e., a non-ceramic, concentrates on the outer surface of the join between the ceramic and the non-ceramic and also in the phenomenon that in certain materials under compressive or tensile stress, the speeds of sound through the materials are different from the corresponding speeds of sound in the absence of such stress. The strength of a join between a ceramic and a non-ceramic is determined by using these phenomena in combination. Namely, according to the present invention, the strength of the join between the ceramic and the non-ceramic is determined by radiating an ultrasonic wave against an outer surface of the join and then measuring the speed of the ultrasonic wave. As a means for the radiation of the ultrasonic wave against the outer surface of the join, the present invention makes use of an ultrasonic microscope which is useful in determining the presence or absence of damage in the surface layer of a material. When a converging ultrasonic beam is radiated against the surface layer of the material, a reflected wave is generated. This reflected wave is an interference wave of a wave, which has been reflected from the material and a radiated wave of an elastic surface wave produced on the surface layer of the material by a particular ultrasonic beam out of the converging ultrasonic beam, said particular ultrasonic beam having struck the surface layer at a critical angle. The intensity of the interference wave varies at a cycle, which is specific to the material, in accordance with variations of the relative distance between the source of the converging ultrasonic beam and the material. Further, the cycle has a certain fixed relationship with the speed of the surface wave. The present invention makes use of a technique which utilizes these facts. According to the present invention, the above-mentioned elastic surface wave is produced in the vicinity of a join between a ceramic and a non-ceramic by means of such an ultrasonic microscope and the speed of the elastic surface wave is measured in terms of the cycle described above.

In a first aspect of the present invention, there is thus provided a method for determining the strength of a join between a ceramic and an associated non-ceramic by an ultrasonic microscope which radiates a converging ultrasonic beam against a sample and can operatively change the relative distance between a probe of the ultrasonic microscope and the sample, whereby the probe receives, at respective predetermined variations of the relative distance, data on the intensities of interference waves of corresponding reflected waves of the converging ultrasonic beam and corresponding radiated waves of elastic surface waves produced on a surface of the sample by the converging ultrasonic beam and then outputs the data. The method comprises:

radiating the converging ultrasonic beam against a point on a surface of the ceramic, said point being a predetermined distance away from the join between the ceramic and the associated non-ceramic;

collecting data on the intensities of interference waves at the respective predetermined variations of the relative distance;

calculating the residual stress at the point on the basis of the cycle of echo intensities of the interference waves for the respective predetermined variations of the relative distance; and determining the strength of the join on the basis the residual stress.

In a second aspect of the present invention, there is also provided a method for determining the strength of a join between a ceramic and a associated non-ceramic by the above ultrasonic microscope. The method comprises:

successively radiating the converging ultrasonic beam against plural points on a surface of the ceramic, said points being set at predetermined small distances from the join between the ceramic and the associated non-ceramic;

collecting data on the intensities of interference waves at the respective predetermined variations of the relative distance; and comparing the cycle of the interference wave at each of the points with that of the interference wave at the adjacent one of the points.

In a third aspect of the present invention, there is also provided a method for determining the strength of a join between a ceramic and an associated non-ceramic by the above ultrasonic microscope. The method comprises:

radiating the converging ultrasonic beam (B) against a predetermined first point on the ceramic, said point being sufficiently remote from the join between the ceramic and the non-ceramic so that no residual stress is considered to exist there;

collecting data on the intensities of interference waves at the respective predetermined variations of the relative distance;

calculating the speed of elastic surface waves at the first point on the basis of the cycle of the interference waves, said cycle having been obtained from the data, and storing the speed as a preset value;

radiating the converging ultrasonic beam against a predetermined second point adjacent to the join on the ceramic and calculating the speed of elastic surface waves at the second point in the same manner as the speed of the elastic surface waves at the first point; and determining whether the latter speed and the preset value fall within a prescribed tolerance.

In the first aspect of the present invention, a converging ultrasonic beam is radiated from the ultrasonic microscope against the point on the surface of the ceramic, said point being the predetermined distance away from the join between the ceramic and the associated non-ceramic, while changing the relative distance between the probe of the ultrasonic microscope and the joined body. Then, there is produced an interference wave of a reflected wave from the ceramic and a radiated wave of an elastic surface wave produced on the surface of the ceramic by the converging ultrasonic beam. This interference wave varies at a particular cycle in accordance with variations of the relative distance. Such interference waves are received by the probe of the ultrasonic microscope and their data are outputted. From the data thus outputted, the cycle of the interference waves is determined. This cycle has a specific relationship with the propagation speed of the elastic surface wave. Since the propagation speed is in a particular relation with stress, the strength at the above point can be determined on the basis of the cycle. It is therefore possible to easily determine the strength in a small region, so that the strength can be determined accurately.

In the second aspect of the present invention, plural points against which a converging ultrasonic beam should be radiated are set in advance. The above-mentioned cycle is successively measured at the respective points. By comparing the cycle at each point with that at the adjacent one of the points, the distribution of residual stress can be determined clearly. The determination of a strength distribution can therefore be performed easily and accurately.

In the third aspect of the present invention, on the side of the ceramic of the joined body, the above-mentioned cycle is measured at a point where no residual stress exists, whereby the propagation speed is determined. The ratio of this propagation speed to a propagation speed determined similarly at a desired point near the join is then calculated. The quality of the joined body is judged by determining whether the above ratio falls within a prescribed tolerance or not. It is accordingly possible to determine whether the joined body can be used or not.

BRIEF DESCRIPTION OF THE DRAWINGS

The above and other objects, features and advantages of the present invention will become apparent from the following description and the appended claims, taken in conjunction with the accompanying drawings, in which:

FIG. 5 is a waveform diagram of interference waves received by a probe when a reference wave was caused to interfere with.

DETAILED DESCRIPTION OF THE INVENTION AND PREFERRED EMBODIMENTS

Figure 1:
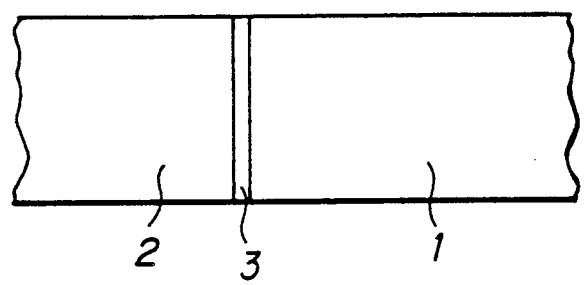
FIG. 1 is a side view of a joined ceramic-Kovar body.
Figure 2:
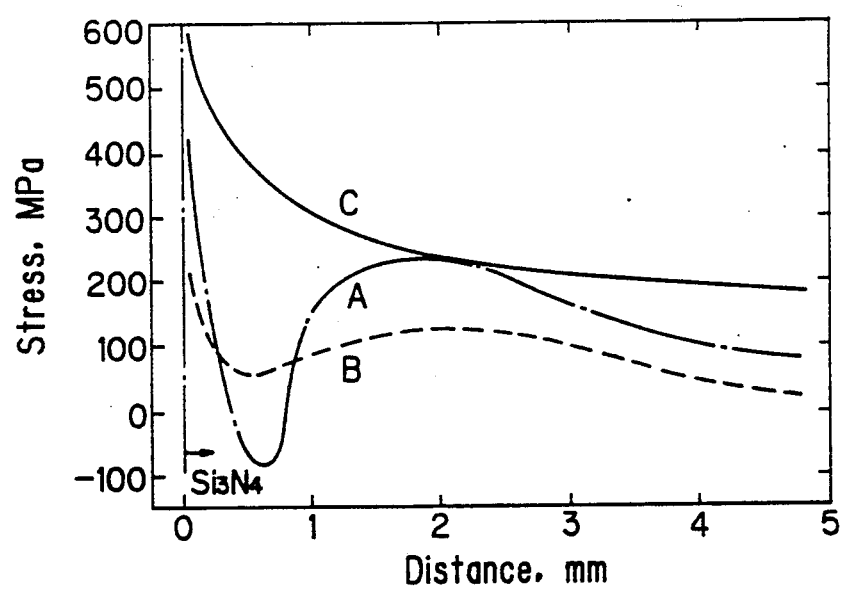
FIG. 2 is a stress distribution diagram of the joined ceramic-Kovar body.
Figure 3:
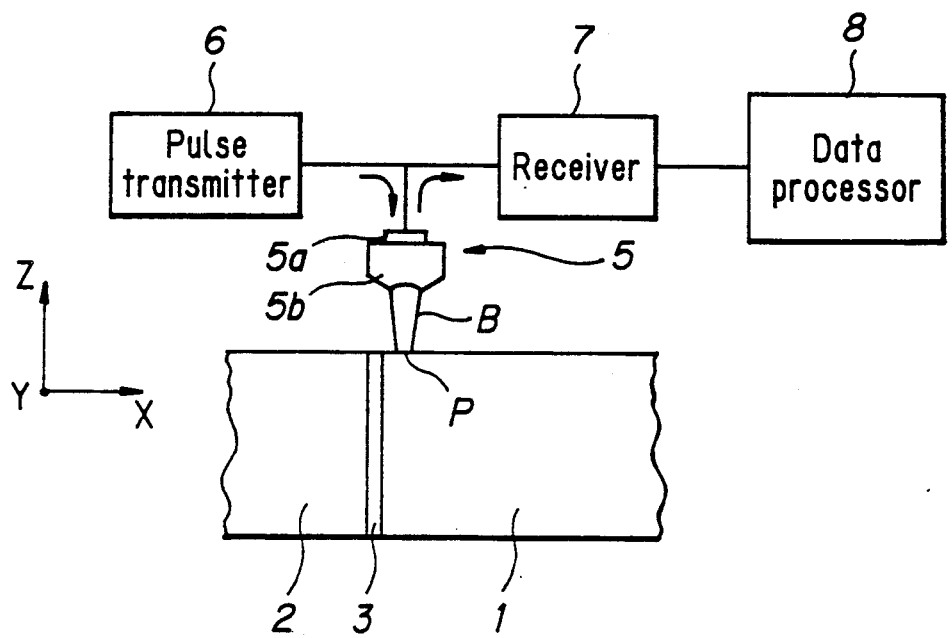
FIG. 3 is a simplified block diagram showing a method according to one embodiment of this invention, which method is useful in determining the strength of a join between a ceramic and a Kovar in a joined ceramic-Kovar body.

Referring first to FIG. 3, the joined body the strength of whose join is to be determined is identical to the joined body illustrated in FIG. 1. Like parts are therefore identified by like numerals. There are also illustrated a probe 5 composed of a piezoelectric thin film 5a and an acoustic lens 5b, a pulse transmitter 6 for outputting pulses to excite the piezoelectric thin film 5a, a receiver 7 for receiving signals form the piezoelectric thin film 5a, and a data processor 8 for processing the signals received by the receiver 7. An ultrasonic microscope is constructed of the probe 5, pulse transmitter 6, receiver 7 and data processor 8. Designated at letter B is an ultrasonic beam whose convergence is produced by the acoustic lens 5b. The acoustic lens 5b is formed in such a way that a converging ultrasonic beam B contains an ultrasonic beam which is radiated at a critical angle. Letter P indicates a point of measurement on the surface of the ceramic 1. Letters X, Y and Z indicate coordinate axes, respectively. Y-axis extends in a direction perpendicular to the drawing sheet. The probe 5 and the joined body are arranged in such a way that both or either one of the probe 5 and the joined body is driven along Z-axis. In addition, a suitable medium, for example, water is interposed between the probe 5 and the joined body.

A description will next be made of the method of the present embodiment for the determination of strength. First of all, the point P is chosen on the surface of the ceramic 1 in the joined body. The point P is a predetermined distance away from the join. It is to be noted that the size of the point P is exaggerated in the drawing. The converging ultrasonic beam B is then radiated against the thus-chosen point P. Namely, when pulses are applied from the pulse transmitter 6 to the piezoelectric thin film 5a, the piezoelectric thin film 5a is excited to generate an ultrasonic wave. This ultrasonic wave is subjected to convergence by the acoustic lens 5b, so that the ultrasonic wave is converted to the converging ultrasonic beam B and is radiated against the point P. This converging ultrasonic beam B becomes a wave reflected by the ceramic 1 and while taking back the same path as the path at the time of radiation, the reflected wave returns to the piezoelectric thin film 5a. By the ultrasonic beam struck at a critical angle out of the converging ultrasonic beam B, an elastic surface wave which advances along the surface of the ceramic 1 is concurrently produced on the surface of the point P of the ceramic 1. A portion of an ultrasonic wave produced by the elastic surface wave and radiating from the surface of the point P also returns to the piezoelectric thin film 5a likewise the reflected wave from the ceramic 1. The ultrasonic wave which returns to the piezoelectric thin film 5a is therefore an interference wave in which the waveform of vibrations of the above reflected wave and that of the radiated wave of the elastic surface wave are superposed. By the sound pressure of the interference wave, the piezoelectric thin film 5a outputs electrical signals (reflection signals) which are proportional to the magnitude of the sound pressure. The reflection signals are fed via the receiver 7 to the data processor 8 and are processed there.

Figure 4:
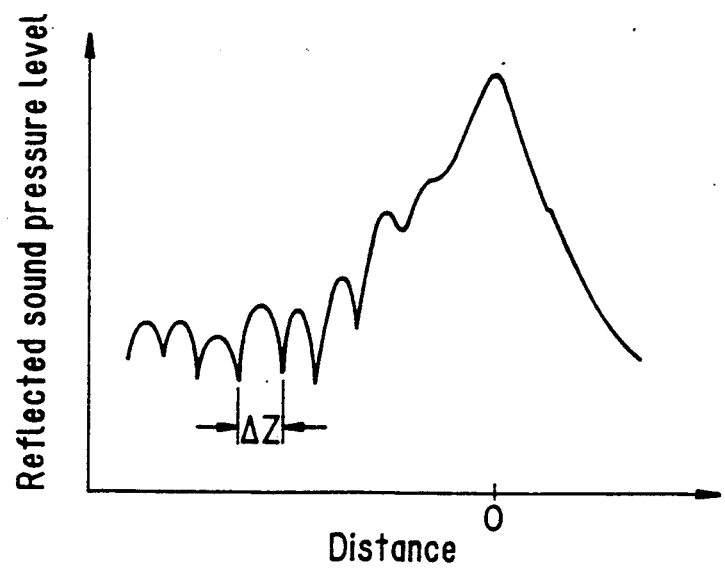
FIG. 4 is a waveform diagram of interference waves received by a probe shown in FIG. 3.

When the probe 5 is adjusted to bring the focal point of the converging ultrasonic beam B into coincident with the point P and the above operation is then conducted while moving the probe 5 toward the ceramic 1 along Z-axis, reflection signals to be outputted from the piezoelectric thin film 5a will have the waveform shown in FIG. 4. In this diagram, distances between the probe 5 and the ceramic 1 in the direction of Z-axis are plotted along the axis of abscissas and reflection signal levels ar plotted along the axis of ordinates. Numeral 0 on the axis of abscissas indicates the position of the probe 5 when the focal point of the converging ultrasonic beam B has been brought into coincident with the surface of the ceramic 1.

As the probe 5 is moved from the position 0 toward the ceramic 1 along Z-axis, the distance between the incident point on the ceramic 1, at which the ultrasonic beam strikes at the critical angle, and the point of radiation (which is located at the position symmetrical to the incident point relative to the center of the converging ultrasonic beam) of the radiated wave of the elastic surface wave produced by the entering of the ultrasonic beam increases. In other words, the travelling distance of the elastic surface wave becomes longer. As a result, more time is required until the ultrasonic beam radiated from the point of radiation reaches the piezoelectric thin film 5a so that a variation occurs in the degree of interference with the reflected wave. As the probe 5 is moved closer to the surface of the ceramic 1, the overlapping of the maximum values and minimum values of the waveforms of vibrations of these two waves varies. As a result, the resultant interference wave has a waveform which has a constant period $\Delta Z$ as shown in the diagram. The wave form obtained in the above-described manner is called a "V(Z) curve". This V(Z) curve is displayed on an unillustrated display unit in the data processor 8.

Incidentally, the period $\Delta Z$ of the above V(Z) curve varies depending on the conditions of a surface layer of a material against which a converging ultrasonic beam is radiated. The relationship represented by the following formula can be established between the period and the propagation speed of an elastic surface wave through the surface layer of the material:

$$V_R = V_W (\Delta Z / \lambda_W)^{\frac{1}{2}} \ldots \quad (1)$$

where
 $\Delta Z$: the period of the V(Z) curve,
 $V_R$: the propagation speed of the elastic surface wave through the surface layer of the material,
 $V_W$: the speed of sound in a medium (water) interposed between the probe 5 and the ceramic 1,
 $\lambda_W$: the wavelength of sound wave in the medium.

Since the speed $V_W$ of sound and the wavelength $\lambda_W$ are known in the above formula, the speed $V_R$ of sound can be found provided that the period $\Delta Z$ is known.

The speed of the elastic surface wave at the point P can be determined, for example, by displaying the V(Z) curve, which has been obtained at the point P on the ceramic 1 shown in FIG. 3, on the unillustrated display unit of the data processor 8 and measuring the period $\Delta Z$. Since there is a constant relationship between speeds of sound and corresponding stresses as described above, determination of the period $\Delta Z$ makes it possible to obtain the residual stress at the point P in accordance with the formula.

Figure 5:
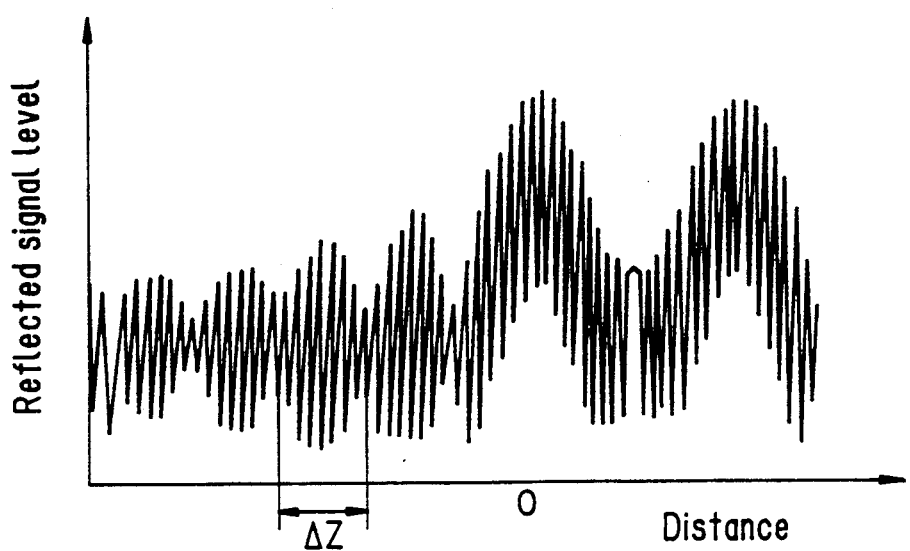

With a view toward achieving accurate determination of the period $\Delta Z$, various methods have been proposed, including the use of a referential waveform having a much shorter period than the period $\Delta Z$. As one example of such methods, a V(Z) curve obtained by having a reference wave of a very short period interfered with is illustrated in FIG. 5. Thus, the V(Z) curve has a waveform interfered with the reference wave. Used as such a reference wave is a reflected wave obtained as a result of reflection of an ultrasonic beam, which has been radiated from the piezoelectric thin film 5a, by the surface of the acoustic lens 1b. This reflected wave is superposed with the reflected wave from the sample and the radiated wave of the elastic surface wave, whereby the interference waveform shown in FIG. 5 is obtained. Similarly to FIG. 4, distances along Z-axis and reflection signal levels are plotted along the axis of abscissas and the axis of ordinates, respectively in FIG. 5. By obtaining such an interference waveform, the period $\Delta Z$ can be determined with high accuracy. As a matter of fact, a variation of the speed of an elastic surface wave under stress is extremely small. It is thus practically impossible to measure this speed variation even if the speed of the elastic surface wave can be measured directly. However, accurate determination of the period $\Delta Z$ as described above makes it possible to accurately determined the variation of the speed of the elastic surface wave too. As a consequence, the residual stress at the point P can be measured with high resolution in the present embodiment.

The method described above is useful in determining the residual stress at the point P. Determination of the residual stress is however not absolutely necessary for the determination of the strength at the point P. If the period $\Delta Z_0$ at a point where the residual stress is 0 is determined in advance with respect to the ceramic 1 or a similar ceramic, the residual stress, namely, the relative level of strength at the point P can be determined only by determining the period $\Delta Z$ at the point P and comparing it with the period $\Delta Z_0$. Accordingly, no calculation is needed for the determination of the residual stress.

Measurement of the residual stress at the point P which is the predetermined distance away from the joined boundary, namely, the determination of strength has been described above. As is readily understood from the foregoing, it is only necessary to perform the above operation successively with respect to predetermined points on the surface of the ceramic 1 to know the distribution of residual stress. If the periods of the adjacent points in a certain area are found to have a constant value and to remain unchanged by the above procedure, the area is determined to be free of residual stress. To determine the distribution of relative strength levels in a ceramic, it is only necessary to determine the periods $\Delta Z$ at predetermined points and then calculating the difference between the thus-determined periods at adjacent points or the ratio thereof. This procedure makes it possible to obtain an accurate strength distribution. Further, extension of determination of such periods to an area where no residual stress exists permits more accurate determination of the strength of the join 3 between the ceramic 1 and the metal 2.

The strength of the join 3 between the ceramic 1 and the metal 2 can also be determined by the following method. Firstly, the period $\Delta Z$ is measured at a point on the ceramic 1 of the joined body, at which point no joining-related residual stress is believed to exist, in other words, at a point sufficiently remote from the join 3. The corresponding speed of sound is then calculated and is used as a preset value $V_0$. A tolerance of the ratio of a speed of sound, which is to be calculated on the basis of a period $\Delta Z$ measured at another point, to the preset value $V_0$ is then preset in view of the manner of use of the joined body and other aspects. Next, the period $\Delta Z$ at a desired point near the join 3 is measured to calculate the speed of sound at the point. Thereafter, the ratio of this speed of sound to the preset value $V_0$ is calculated. Based on this ratio, the relative strength at the desired point can be determined. A judgment is next made as to whether the ratio thus determined falls within the tolerance. If it is within the tolerance, a similar operation is conducted with respect to another desired point. If it is outside the tolerance, the joined body is judged to be unusable. In this manner, it is possible not only to determine the relative strength of the joined body but also to judge whether the joined body can be used or not.

As has been described above, in the present embodiment, a converging ultrasonic beam is radiated from an ultrasonic microscope against a predetermined point on a ceramic of a joined ceramic-metal body and the period of an interference wave of a reflected wave of the converging ultrasonic wave and a radiated wave of the resulting elastic surface wave is determined. It is hence possible to determine the period in a region as small as only slightly larger than the size of the converging ultrasonic beam at the focal point thereof. It is accordingly possible to easily measure the residual stress in such a small region or to easily determine the strength in such a small region. Further, the residual stress is calculated on the basis of the period of the interference wave, which period can be accurately measured. It is therefore possible to obtain high resolution. The results of an exemplary experiment conducted using the method of this embodiment will hereinafter be described with reference to FIG. 6.

Figure 6:
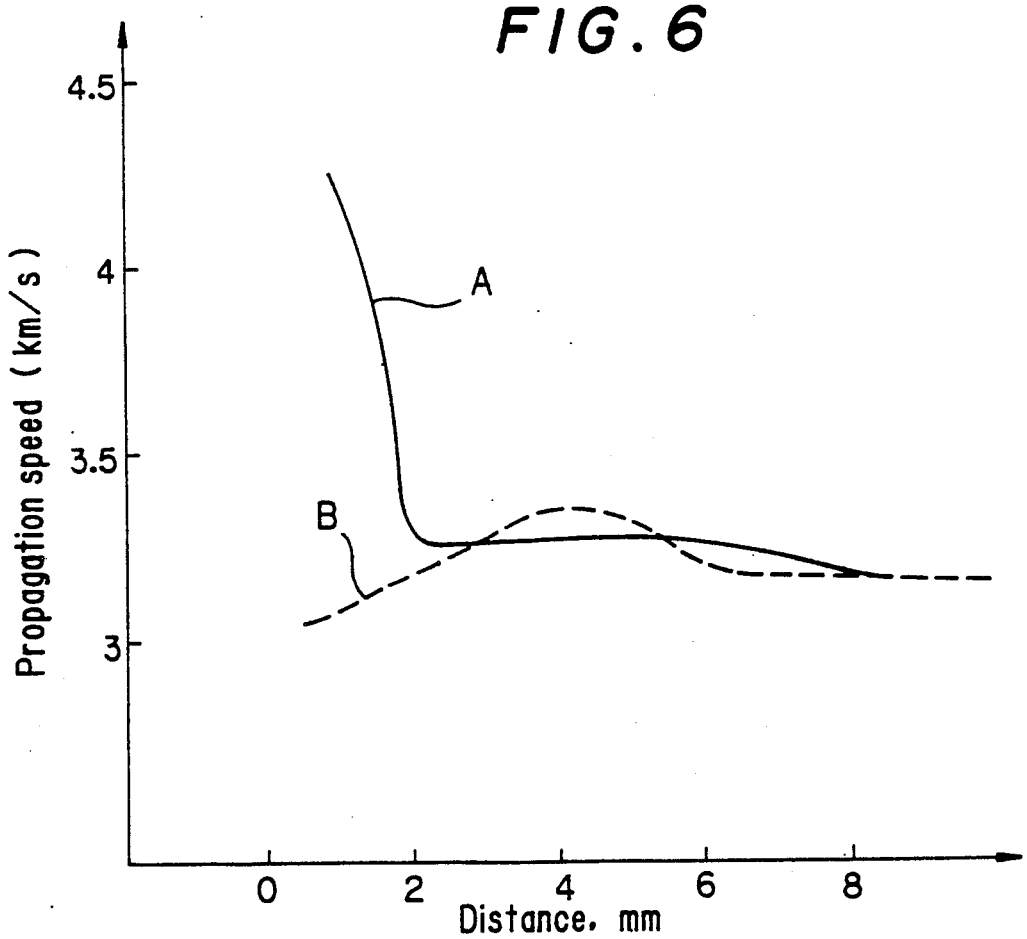
FIG. 6 is a distribution diagram of propagation speeds of surface waves.

FIG. 6 shows the distribution diagram of propagation speeds calculated in accordance with the formula (1), based on the measured periods of interference waves.

Distances from the join are plotted along the axis of abscissas, while propagation speeds are plotted along the axis of ordinates. Distribution curve A indicated by a solid curve represents the distribution of propagation speeds in a joined body in which Kovar and a ceramic are bonded together directly. Distribution curve B indicated by a dashed curve shows the distribution of propagation speeds in a joined body in which Kovar and a ceramic are bonded together using nickel as an intermediate material. In the case of the former bonded body featuring the direct bonding of Kovar and the ceramic, high speeds of sound are observed in an area close to the join. It is hence envisaged that the residual stress is large, in other words, the strength is weak in this area and the speed of sound drops abruptly to a constant level as the distance becomes greater from the join. On the other hand, in the case of the latter joined body featuring the joining with the intermediate nickel material, relatively low speeds of sound are observed in an area close to the join. It is also observed that the speed of sound once increases and then decreases to a constant level. In each of the cases, the speed of sound in a area sufficiently remote from the join is in conformance with the speed of sound across the ceramic itself (i.e., the speed of sound across the ceramic in which no residual stress exists). The advantageous effects of the use of nickel as an intermediate material can be clearly envisaged from the above distribution diagram.

What is claimed is:

1. A method for determining the strength of a join between a ceramic and an associated non-ceramic by an ultrasonic microscope which radiates a converging ultrasonic beam against a sample and can operatively change the relative distance between a probe of the ultrasonic microscope and the sample, whereby the probe receives, at respective predetermined variations of the relative distance, data on the intensities of interference waves of corresponding reflected waves of the converging ultrasonic beam and corresponding radiated waves of elastic surface waves produced on a surface of the sample by the converging ultrasonic beam and then outputs the data, which method comprises:

radiating the converging ultrasonic beam against a point on a surface of the ceramic, said point being a predetermined distance away from the join between the ceramic and the associated non-ceramic;

collecting data on the intensities of interference waves at the respective predetermined variations of the relative distance;

calculating the residual stress at the point on the basis of the cycle of echo intensities of the interference waves for the respective predetermined variations of the relative distance; and determining the strength of the join on the basis of the residual stress.

2. A method for determining the strength of a join between a ceramic and an associated non-ceramic by an ultrasonic microscope which radiates a converging ultrasonic beam against a sample and can operatively change the relative distance between a probe of the ultrasonic microscope and the sample, whereby the probe receives, at respective predetermined variations of the relative distance, data on the intensities of interference waves of corresponding reflected waves of the converging ultrasonic beam and corresponding radiated waves of elastic surface waves produced on a surface of the sample by the converging ultrasonic beam and then outputs the data, which method comprises:

successively radiating the converging ultrasonic beam against plural points on a surface of the ceramic, said points being set at predetermined small distances from the join between the ceramic and the associated non-ceramic;

collecting data on the intensities of interference waves at the respective predetermined variations of the relative distance; and comparing the cycle of the interference wave at each of the points with that of the interference wave at the adjacent one of the points.

3. A method for determining the strength of a join between a ceramic and an associated non-ceramic by an ultrasonic microscope which radiates a converging ultrasonic beam against a sample and can operatively change the relative distance between a probe of the ultrasonic microscope and the sample, whereby the probe receives, at respective predetermined variations of the relative distance, data on the intensities of interference waves of corresponding reflected waves of the converging ultrasonic beam and corresponding radiated waves of elastic surface waves produced on a surface of the sample by the converging ultrasonic beam and then outputs the data, which method comprises:

radiating the converging ultrasonic beam against a predetermined first point on the ceramic, said point being sufficiently remote from the join between the ceramic and the non-ceramic so that no residual stress is considered to exist there;

collecting data on the intensities of interference waves at the respective predetermined variations of the relative distance;

calculating the speed of elastic surface waves at the first point on the basis of the cycle of the interference waves, said cycle having been obtained from the data, and storing the speed as a preset value;

radiating the converging ultrasonic beam against a predetermined second point adjacent to the join on the ceramic and calculating the speed of elastic surface waves at the second point in the same manner as the speed of the elastic surface waves at the first point; and determining whether the latter speed and the preset value fall within a prescribed tolerance.

* * * * *